United States Patent [19]

Tsao et al.

[11] Patent Number: 5,869,274

[45] Date of Patent: Feb. 9, 1999

[54] IMMUNO-HISTOCHEMICAL METHOD THAT REDUCES BACKGROUND STAINING

[75] Inventors: Dean Tsao, Hillsborough; Zuo-Rong Shi, Redwood City; Peter Luu, Clayton, all of Calif.

[73] Assignee: Zymed Laboratories, Inc., South San Francisco, Calif.

[21] Appl. No.: 891,238

[22] Filed: Jul. 10, 1997

Related U.S. Application Data

[63] Continuation of Ser. No. 513,062, Aug. 9, 1995, abandoned.
[51] Int. Cl.[6] ........................ G01N 33/53; G01N 33/537; G01N 33/543
[52] U.S. Cl. .......................... 435/7.92; 435/6; 424/136.1; 530/317
[58] Field of Search ................... 435/7.92, 6; 424/136.1; 530/317

[56] References Cited

U.S. PATENT DOCUMENTS

| | | | |
|---|---|---|---|
| 4,780,406 | 10/1988 | Dolbeare et al. | 435/6 |
| 4,885,237 | 12/1989 | Evans et al. | 435/6 |
| 5,084,378 | 1/1992 | Crissman et al. | 435/6 |
| 5,219,837 | 6/1993 | Cohen et al. | 514/12 |
| 5,334,708 | 8/1994 | Chang et al. | 530/391.5 |
| 5,496,549 | 3/1996 | Yamazaki et al. | 424/158.1 |
| 5,541,287 | 7/1996 | Yau et al. | 530/317 |
| 5,571,675 | 11/1996 | Baker et al. | 435/6 |
| 5,601,819 | 2/1997 | Wong et al. | 424/136.1 |
| 5,643,727 | 7/1997 | Reed et al. | 435/6 |

OTHER PUBLICATIONS

Nielsen et al., "A method for the blocking of endogenous immunoglobulin on frozen tissue sections in the screening of human hybridoma antibody in culture supernatants" *Hybridoma* (1987) 6:103–109.

Foulds et al., "The use of fab fragments in a screening method for the detection of human anti–tumor monoclonal antibodies" *Hybridoma* (1988) 9:91–96.

Brandon, "Improved immunocytochemica staining through theuse of fab fragments of primary antibody, fab–specific second antibody, and fab–specific second antibody, and fab–horseradish peroxidsae" *J of Histochemistry and Cytochemistry* (1985) 33(7):715–719.

Burgess, et al. "Two–colour immunoenzymatic technique using sequential staining by APAAP to evaluate two cell antigens" *J Clin Path* (1992) 45:206–209.

Carayon, et al. "Identification of DNA–replicating lymphocyte subsets using a new method to label the bromo–deoxyuridine incorporated into the DNA" *J of Immunological Methods* (1992) 147:225–230.

Ffrench, et al. "Choice of fixation and denaturation for the triple labelling of intra–cytoplasmic antigen, bromodeoxyuridine and DNA" *Histochemistry* (1994) 101:385–390.

Foulds et al., "The use of fab fragments in a screening method for the detection of human anti–tumor monoclonal antibodies" *Hybridoma* (1988) 9:91–96.

Gratzner, et al. "The use of antibody specific for bromodeoxyuridine for the immunofluorescent determination of DNA replication in single cells and chromosomes" *Experimental Cell Research* (1975) 95:88–94.

Montuenga, et al. "Simultaneous immunostaining method for localization of bromodeoxyuridine and calcitonin gene–related peptide" *J of Histochemistry and Cytochemistry* (1992) 40(8):1121–1128.

Muir, et al. "An enzyme linked immunosorbent assay for bromodeoxyuridine incorporation using fixed microcultures" *Analytical Biochemistry* (1990) 185:377–382.

Negoescu, et al. "F(ab) secondary antibodies: A general method for double immunolabeling with primary antisera from the same species. Efficiency control by chemiluminescence" *J of Histochemistry and Cytochemistry* (1994) 42(3):433–437.

Nielsen et al., "A method for the blocking of endogenous immunoglobulin on frozen tissue sections in the screening of human hybridoma antibody in culture supernatants" *Hybridoma* (1987) 6: 103–109.

Soriano, et al. "Simultaneous immunocytochemical visualization of bromodeoxyuridine and neural tissue antigens" *J of Histochemistry and Cytochemistry* (1991) 39(3):255–263.

Toba et al., "Improved staining method for the simultaneous flow cytoflurometric analysis of DNA content, s–phase fraction, and surface phenotye using single laser instrumentation" *Cytometry* (1992) 13:60–67.

Giordano, M et al, 1991, Leukemia Res., vol. 15(11), pp. 965–974.
Carayon, P et al, J. of Immunol. Methods, vol. 147, 1992, pp. 225–230.
Soriano et al, J Histochem Cytochem, vol. 39, #3, pp. 255–263, 1991.
Montuenga et al, J Histochem Cytochem, vol. 40, #8, pp. 1121–1128, 1992.
Brandon, C, J Histochem Cytochem, vol. 33, #7, pp. 715–719, 1985.
Ffrench, et al, Histochemistry, vol. 101, pp. 385–390, 1994.
Toba et al, Cytometry, vol. 13, pp. 60–67. 1992.
Negoescu et al, J Histochem Cytochem, vol. 42, #3, pp. 433–437, 1994.
Muir et al, Analytical Biochem. vol. 185, pp. 377–382, 1990.
Carayon et al, J Immunolog Meth., vol. 147, pp. 225–230, 1992.
Burgess et al, J Clin. Path., vol. 45, pp. 206–209, 1992.
Gratzner et al, Exp. Cell Research, vol. 95, pp. 88–94, 1975.

*Primary Examiner*—James C. Housel
*Assistant Examiner*—Ginny Allen Portner
*Attorney, Agent, or Firm*—Morrison & Foerster LLP

[57] ABSTRACT

The embodiments of the invention are multiple antibody immunoassay systems, and preferably immunohistochemical staining systems. In these systems the detection antibody system that detects the association of a targeting antibody (that binds to the target moiety to be detected) may also cross-react with endogenous immunoglobulins in the specimen in which the target moiety is to be detected, yielding an unreliable assay with high background levels. This problem has been overcome by a process that includes cross-linking a monovalent antibody to the endogenous antigenic determinants prior to exposure to the targeting antibody and detecting antibody system. The embodiments of the invention also include kits for use in these multiple antibody immunoassay and histochemical staining systems.

10 Claims, 1 Drawing Sheet

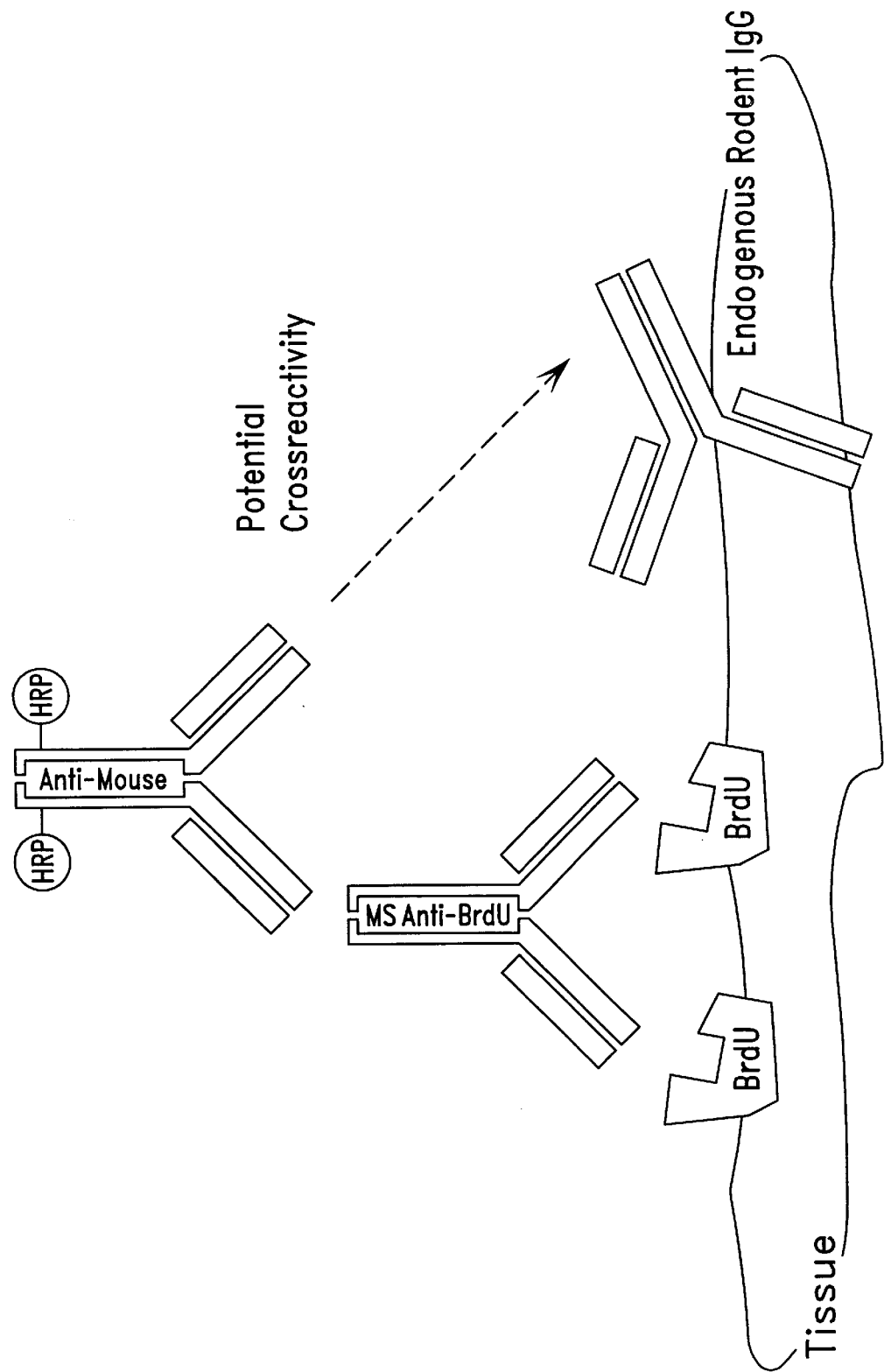

IMMUNO-HISTOCHEMICAL METHOD THAT REDUCES BACKGROUND STAINING

This application is a continuation of application Ser. No. 08/513,062, filed Aug. 9, 1995, now abandoned.

FIELD OF INVENTION

This invention pertains to immunoassays and more particularly to immuno-histochemical staining techniques.

BACKGROUND OF THE INVENTION

In some immuno-histochemical detection systems a target antigen present in the histology sample is detected by a double antibody system. Initially the sample is incubated with a primary targeting antibody that is specific for the target antigen. Detection of antigen-antibody complexes containing the primary antibody and formed during the first incubation is accomplished by incubation with a second detecting antibody that binds to a region of the constant domain in the primary antibody; the second antibody is labeled. The result of the second incubation is, in the presence of the target antigen, a complex of antigen and layers of antibodies that contain the label.

A problem arises in these staining processes when both the targeting antibody (that binds to the target antigen to be detected) and the specimen in which the antigen is to be detected are from the same or related species. Under these conditions, due to the homology of antigenic determinants on the targeting antibody and tissue, the detecting antibody reacts with endogenous antigenic determinants in the tissue causing significant background staining, thus reducing the usefulness of the assay.

Prior attempts to reduce non-specific background in homologous staining systems have used Fab' fragments to block the recognition of the tissue antigenic determinants. When a human anti-tumor antibody was used to stain human tissue sections, Fab' fragments of anti-human antibody were incubated with the tissue section prior to incubation with the targeting primary antibody and secondary detecting antibody. Nielsen et al. (1987) used Fab' rabbit anti-human IgG and Fab' rabbit anti-human IgM as blockers and reported successful blocking with the IgM system, but the background was not abolished in the IgG system. Nielsen, B. et al. (1987), Hybridoma 6:103. Foulds et al. attempted to improve the Fab' blocking process with a prolonged washing step of 20 hours. Foulds, S. and Eremin, O (1988), Hybridoma 9:91.

BRIEF SUMMARY OF THE INVENTION

The invention described herein provides a solution to the problem of non-specific antibody binding in multiple antibody immunoassay systems, including immunohistochemical systems. In the processes of the invention endogenous non-specific antibody binding sites on tissue containing a target moiety to be detected are blocked by monovalent antibodies that are specifically cross-linked to these non-specific binding sites. The result is a drastic reduction and elimination of background binding. This method is particularly useful in immunohistochemical staining methods to reduce the level of background staining.

Accordingly, embodiments of the invention include the following.

An immunoassay method for detecting a target moiety in a biological sample, wherein the detecting utilizes a targeting antibody that associates with the target moiety, and a detecting antibody system containing a label that detects the presence of the targeting antibody, and wherein the biological sample contains an antigenic determinant recognized by at least one antibody in the detecting antibody system, the method comprising:

(a) providing a targeting antibody that can associate with the target moiety;

(b) providing a detecting antibody system comprised of an antibody that is associated with a label, wherein the system detects the targeting antibody;

(c) providing a monovalent antibody that recognizes an antigenic determinant in a biological sample suspected of containing a target moiety, which antigenic determinant is also recognized by the detecting antibody system;

(d) incubating the biological sample suspected of containing a target moiety with the monovalent antibody of (c) under conditions that allow immunological binding to the biological sample and removing excess monovalent antibody;

(e) applying a reagent that cross-links an immunological complex containing the monovalent antibody formed in step (d), and removing excess reagent;

(f) incubating the biological sample from step (e) with the targeting antibody of step (a) under conditions that allow association of the targeting antibody with the target moiety, if any, and removing excess targeting antibody;

(g) incubating the biological sample from step (f) with the detecting antibody system of step (b) under conditions that allow immunological binding; and (h) detecting complexes containing a label associated with the detecting antibody of step (b), if any.

The above-described immunoassay wherein the biological sample is affixed to a solid substrate.

The above described immunoassays wherein the cross-linking reagent is an aldehyde. The aldehyde may be selected from the group consisting of paraformaldehyde, glutaraldehyde, and formaldehyde.

An immunohistochemical method for detection of a target antigen in a tissue sample wherein the detecting utilizes a targeting antibody that associates with a target moiety, and a detection antibody system containing a label that detects the presence of the targeting antibody, and wherein the tissue contains an antigenic determinant recognized by at least one antibody in the detecting antibody system, the method comprising:

(a) providing a targeting antibody that can associate with the target moiety;

(b) providing a detecting antibody system comprised of an antibody that is associated with a label, wherein the system detects the targeting antibody;

(c) providing a monovalent antibody that recognizes an antigenic determinant in a tissue sample suspected of containing a target moiety, which antigenic determinant is also recognized by the detecting antibody system;

(d) incubating tissue suspected of containing a target moiety with the monovalent antibody of (c) under conditions that allow immunological binding to the tissue and removing excess monovalent antibody from the tissue;

(e) applying a reagent that cross-links an immunological complex containing the monovalent antibody formed in step (d), and removing excess reagent;

(f) incubating the tissue from step (e) with the targeting antibody of step (a) under conditions that allow association of the targeting antibody with the target moiety, if any, and removing excess targeting antibody;

(g) incubating the tissue from step (f) with the detecting antibody system of step (b) under conditions that allow immunological binding; and (h) detecting by the presence of the label complexes containing the antibody of step (b).

The above-described immunohistochemical method wherein the label is an enzymic moiety. The enzymic moiety in the presence of enzyme substrate catalyzes a reaction yielding a product that stains tissue, and a complex containing the detecting antibody is detected by the presence of stain.

The above-described immunohistochemical method wherein the enzymic moiety catalyzes a horseradish peroxidase reaction.

A kit for use in an above-described immunoassay method comprising in suitable packaging: a monovalent antibody that can bind immunologically to immunoglobulin of a biological sample to be tested for a target moiety; and a cross-linking reagent appropriate for use with the antibody.

The above-described kit further comprising a detecting antibody system comprising a detecting antibody containing a label.

A kit for use in an immunohistochemical method to detect a target moiety in tissue comprising in suitable packaging: a species specific monovalent antibody that can bind immunologically to immunoglobulin of tissue to be tested for a target moiety; a cross-linking reagent appropriate for use with the antibody; and a detecting antibody system comprised of an antibody containing a label.

The above described kit wherein the label is an enzymic moiety and the kit is further comprised of substrate that produces a detectable product when acted upon by the enzymic moiety.

The above-described kits wherein the tissue to be tested is rodent tissue and the monovalent antibody is directed an antigenic determinant on rodent immunoglobulin.

The above-described kits wherein the tissue to be tested is human tissue and the monovalent antibody is directed an antigenic determinant on human immunoglobulin.

BRIEF DESCRIPTION OF THE DRAWINGS

FIG. 1 is a diagram illustrating the probable cause of high background levels in immunohistochemical staining of BrdU labeled DNA rodent tissue using a rodent targeting antibody and a horseradish peroxidase labeled anti-mouse detecting antibody.

MODES OF CARRYING OUT THE INVENTION

The following terms when used herein are defined as follows.

A "multiple antibody immunoassay system" is an immunoassay system in which at least two antibodies are used to detect a "target" moiety: a primary targeting antibody that associates with the targeted moiety; and a detecting antibody system that via at least one immunological reaction detects the presence of the primary antibody.

A "targeting" antibody is an antibody that contains a targeting moiety that will, under appropriate conditions, allow association of the targeting antibody with the targeted moiety in the sample being tested. Examples of the targeting antibody moieties include, for example, cytokines, hormones, adhesion molecules, the paratope of the antibody, and lectins, that could be used to bind to cytokine receptors, hormone receptors, adhesion molecule receptors, antigenic determinants, and glycoproteins, respectively. Thus, the targeting antibody may, but does not necessarily rely on immunologic recognition of the targeted moiety. The targeting antibody may also be referred to as the "primary antibody".

A "detection" antibody system (also called a "detecting" antibody system) contains a label associated with an antibody that recognizes an antigenic determinant associated with a targeting antibody; the antigenic determinant may be one on the targeting antibody itself, or on a moiety associated with the targeting antibody, for example, another polypeptide (e.g., an intermediate antibody that binds to the targeting antibody). Generally, the antibody containing the label is the "detecting" antibody, and detection of the target antigen is accomplished by determining the presence of the label after incubating the sample with the targeting antibody and detection antibody system.

An "epitope" also called "an antigenic determinant" is the structure on an antigen that interacts with the combining site of an antibody or a T cell receptor as a result of molecular complementarity.

A "paratope" is an antibody combining site for an epitope.

A "target" moiety is the moiety to be detected by the association of the primary targeting antibody with it.

An "antibody" (interchangeably used in plural form) is an immunoglobulin molecule capable of specific binding to a target, such as a polypeptide, through at least one antigen recognition site, located in the variable region of the immunoglobulin molecule. As used herein, the term encompasses not only intact antibodies, but also fragments thereof, mutants thereof, fusion proteins, recombinant antibodies, humanized antibodies, and any other modified configuration of the immunoglobulin molecule that comprises an antigen recognition site of the required specificity.

A "monovalent antibody" refers to an antibody molecule that contains only one paratope or antigen binding region. Fab, Fab', and single chain antibodies are examples of a monovalent antibody.

A "multivalent antibody" is an antibody molecule that contains two or more antigen binding regions.

"Constant region" refers to a relatively invariant part of the immunoglobulin heavy and light chains and of the antigen binding regions of the T cell receptor.

"Variable domain" also called "variable region" refers to the N-terminal region of antibody heavy and light chains and the $\alpha$ and $\beta$ chains of the T cell receptor which vary between different clones of antibodies, and that form the antigen-binding site.

"Immunological recognition" or "immunological reactivity" refers to the specific binding of a target through at least one antigen recognition site in an immunoglobulin or a related molecule, such as a B cell receptor or a T cell receptor.

The term "antigen" refers to a target molecule that is specifically bound by an antibody through its antigen recognition site. The antigen may be polyvalent, or it may be a monovalent hapten. Examples of kinds of antigens that can be recognized by antibodies include polypeptides, polynucleotides, other antibody molecules, oligosaccharides, complex lipids, drugs, and chemicals.

As used herein the term "biological sample" includes samples of bodily fluids of an individual (e.g., blood, sputum, lymph, sweat, urine, semen, etc.), tissue samples, cells, cell cultures and supernatants obtained therefrom.

The term "tissue" refers to a naturally occuring agglomeration of cells.

The invention provides a solution to the problem of high background levels that cause unreliability in multiple antibody immunoassay systems. These high background levels result when the detecting antibody system that detects the presence of the targeting antibody also recognizes antigenic determinants on the specimen being tested.

An example of when this type of problem arises when the specimen containing the targeted moiety and targeting antibody are from homologous species. The diagram in FIG. 1 illustrates the problem. In FIG. 1 BrdU labeled DNA in rodent tissue is detected by immunohistochemical staining. The targeting antibody is mouse anti-BrdU, and the detecting antibody system uses an anti-mouse immunoglobulin antibody, labeled with horse radish peroxidase ("HRP"). Because there is homology between mouse immunoglobulin and immunoglobulins from other species from a number of rodent species (for example, rats, mice, hamsters, etc.), the detecting antibody not only binds to the targeting antibody, but also non-specifically binds to immunoglobulin in the tissue.

A similar problem could arise if, for example, a humanized mouse immunoglobulin is used to detect a target moiety on human tissue, and the detection antibody system utilizes an anti-human Ig.

In the processes of the invention non-specific binding to the target tissue is overcome by incubating the tissue containing the target moiety with a monovalent antibody that binds to the non-specific binding sites on the tissue being tested for the target antigen. These non-specific binding sites may be endogenous immunoglobulins ("Ig"s) on the tissue. The reaction with the monovalent antibody is under conditions that allow the immunological binding of the monovalent antibody to the tissue. A monovalent antibody is preferred because it allows binding to the tissue without the bridging effect of a multivalent antibody molecule. However, the binding of an antibody to antigen is an equilibrium process. A bound monovalent antibody is usually displaced by a multivalent anti-immunoglobulin antibody that is used in the detection process, particularly if the multivalent anti-immunoglobulin is used at high concentrations. Thus, in the processes of the invention, subsequent to its immunological binding to the tissue immunoglobulins, the monovalent antibody is cross-linked to the tissue. Excess monovalent antibody is removed prior to reacting the tissue with the detecting antibody system, and preferably prior to the reacting with the targeting antibody directed to the target moiety.

Monovalent monoclonal antibodies used in the process can be prepared by any procedure known in the art. For example, they may be prepared from immunoglobulin ("Ig") molecules exhibiting the desired specificity. The basic structure of Ig is tetrameric consisting of two identical light and two identical heavy, carbohydrate-containing chains. There are two types of light chain, κ and λ, each of which can be associated with any of five types of heavy chain, $\mu$, $\gamma$, $\alpha$, or $\eta$ corresponding to the class of Igs, A, D, E, G, or M, respectively. Papain treatment of Ig releases monovalent antigen-binding fragments, Fab and a complement binding, Fc fragment. The Fab may be purified from the Fc fragment by procedures known in the art. Alternatively, monovalent antibodies may be prepared by pepsin cleavage, which releases a bivalent antigen-binding $F(ab')_2$ fragment and a complement-binding Fc' fragment. The $F(ab')_2$ fragment can be dissociated by thiol reagents into monovalent fragments.

Methods of producing monovalent antibodies by expression of recombinant polynucleotides resulting in the production of recombinant single chain antibodies ("ScFv") are also known in the art.

The reagents used for cross-linking the monovalent antibody to the tissue to which it is immunologically bound are chemicals which can covalently modify protein molecules so that the cross-linked molecules are in a chemically stable complex that will not come apart under physiological conditions. These compounds may form networks that trap the monovalent antibody with the tissue antigenic determinants to which they are bound, thus rendering the endogenous antigenic determinants inaccessible to subsequent antibodies. These reagents, however, allow the ultrastructure of the tissue and the target antigens to remain in a form in which the target antigens are recognizable by the targeting antibodies. Chemicals fulfilling these requirements are known to those of skill in the art. For example, the cross-linking reagent may include any of the following: an aldehyde (e.g., glyoxal, malondialdehyde, succinaldehyde, glutaraldehyde, adipaldehyde, O-phthaldehyde, formaldehyde); a bisimidate (e.g., diethyl malonimidate, dimethyl malonimidate, dimethyl succinimidate, dimethyl glutarimidate, dimethyl adipimidate); bis-N-succinimidyl esters (e.g., succinate bis-CN-hydroxysuccinimide ester), disuccinimidyl suberate, disuccinimidyl tartarate); aryl halides (e.g., 1,5-difluoro-2, 4-dinitrobenzene; 1,5-dichloro-2,4-dinitrobenzene, 1,5-dibromo-2,4-dinitrobenzene cyanuric acid); and diisocyanates or diisothiocyanates (e.g., dicyclohexylmethane-4,4,'-diisocyanate, ρ-phenylene-diisothiocyanate). Preferred examples of cross-linking reagents include paraformaldehyde, glutaraldehyde, and formaldehyde.

Conditions for the cross-linking reaction may be somewhat dependent upon the cross-linking reagent. However, reagents and conditions are chosen which allow the tissue ultrastructure to remain relatively intact. In addition, it is preferable to choose reagents and conditions which allow a relatively short incubation time for the cross-linking reaction. Generally, the incubation time will be less than 8 hours, preferably less than 4 hours, even more preferably less than 2 hours, and usually between 1 minute and 1 hour.

After the cross-linking of the monovalent antibody, the tissue suspected of containing the target moiety is incubated with the targeting antibody under conditions that allow the association or binding of the targeting antibody to the targeted moiety, if any are present in the tissue. Excess antibody is removed, and complexes containing the targeting antibody are detected by incubation with a detecting antibody system that contains a label. The detecting antibody system contains an antibody that binds to an antigenic determinant on the targeting antibody. This antibody of the detecting antibody system may be the detecting antibody containing a label. However, it may be desirable to use an intermediate between the targeting antibody and the detecting antibody, in which case the detecting antibody recognizes an antigenic determinant on the intermediate. Incubation with the detecting antibody is under conditions that allow the immunological binding of the detecting antibody to the antigenic determinant to which it is directed. The detecting antibody contains a label that allows the determination of its presence in an immunological complex.

Labels suitable for antibodies are known in the art. These include, for example, radioactive moieties, moieties that catalyze enzymic reactions causing the formation of detectable products, and moieties that yield fluorescence.

In a preferred embodiment the multiple antibody immunoassay is a histochemical staining method. In this embodiment the process comprises the following steps. Providing affixed to a solid substrate, preferably a transparent or translucent slide, a tissue specimen suspected of containing a target antigen, and incubating the specimen with a monovalent anti-Ig antibody, wherein the monovalent anti-Ig antibody is directed towards endogenous immunoglobulins of the tissue specimen. Subsequently excess monovalent antibody is removed. The tissue is then treated with a cross-linking reagent under conditions that allow cross-linking of immunological complexes formed from the tissue antigen and the monovalent antibody, and excess cross-linking reagent is removed. The tissue is then incubated with the targeting antibody under conditions that allow its association with the target moiety. After removal of excess targeting antibody, the tissue is incubated with a detecting antibody system containing label, wherein the detecting antibody system contains an antibody that recognizes an antigenic determinant on the targeting antibody. All of the incubations with the detection antibody system are under conditions that allow the formation of an immunological complex. The presence of the label indicates the presence of detecting antibody in a complex with the targeting antibody, which in turn is associated in a complex with the target moiety. In immunohistochemical methods preferred labels are those that cause staining of the tissue when the detecting antibody is present. For example, the detecting antibody may be labeled with an enzyme that catalyzes a reaction yielding a product that causes a detectable stain. If this type of label is used, after incubation with the detecting antibody, the tissue will be further incubated with a substrate for the enzymic reaction, and the presence of the product determined.

The enzyme label used in this type of histochemical method is one that is either absent from or has low endogenous activity in the tissue sample tested. Examples of these types of enzyme labels are known in the art, and include, e.g. horse radish peroxidase.

In a particular embodiment of the process, the tissue suspected of containing a target moiety is a human tumor tissue section and the targeting antibody is a human antibody specific for a defined tumor marker. In another, particular embodiment of the process, the tissue is human liver and the targeting antibody is specific for human DNA.

The embodiments of the invention includes kits that are useful for carrying out the processes of the invention. The kits are comprised of the following reagents in suitable packaging: a species specific monovalent antibody, preferably a Fab fragment, that can bind immunologically to immunoglobulin of the tissue suspected of containing a target moiety and a cross-linking reagent appropriate for use with the antibody. The kit may also be comprised of any of the following ingredients: a detecting antibody containing a label, preferably an enzyme label for immunohistochemical staining; and substrate for the enzymic reaction. Preferably the kit will also contain instructions for the use of the reagents included therein.

The examples presented below are provided as a further guide to a practitioner of ordinary skill in the art, and are not meant to be limiting in any way.

EXAMPLES

The materials used in the Examples are those described below.
Cross-linkers:
  1. Paraformaldehyde
  2. Glutaraldehyde
  3. Formaldehyde Antibodies:
  Primary antibody: Mouse anti-BrdU
  Secondary antibody: Biotin Goat anti-mouse immunoglobulins; Peroxidase associated with streptavidin.
  Blocking antibody: Fab fragment goat anti-mouse immunoglobulins
  Fab Fragment of Goat Anti-Mouse Antibody: Jackson ImmunoResearch Laboratories, Inc., West Grove, Penn.; or alternatively, as prepared in Example 5.
Tissues:
  Mouse small intestine tissue: alcohol or formalin fixed/paraffin embedded tissue. Mouse colon tissue: alcohol or formalin fixed/paraffin embedded tissue
Microscope:
  Nikon labophot microscope with Plan AP 10/0.25 and Plan AP 20/0.75 objective lenses
Solutions:
  Xylene
  100% ethanol
  95% ethanol (v/v): 95% ethanol and 5% reagent water
  80% ethanol (v/v): 80% ethanol and 20% reagent water
  3% H2O2 in methanol (v/v): 3% $H_2O_2$ and 97% methanol
Washing buffer:
  10 mM phosphate buffered saline, pH 7.4
Antibody diluent:
  10 mM phosphate buffered saline, pH 7.4 containing 1% bovine serum albumin and 0.05% sodium azide
Reagents
  Reagents were purchased from a number of sources including Aldrich Chemical Co., Milwaukee, Wis., Sigma Chemical Co., St. Louis, Mo., Fisher Scientific, Pittsburgh, Penn.
Histological Detection and Staining Kit
  Zymed's HistoMouse™ SP Kit, Catalog 95–9541, Zymed Laboratories Inc., South San Francisco, Calif.

EXAMPLE 1

Effect of Conventional Blocking Agents on Background Staining

This example illustrates that background staining is not eliminated by the presence of various blocking reagents commonly used in immunohistochemical techniques.

The tissues were either alcohol fixed or formalin fixed, BrdU treated mouse small intestine. The detection system was a commercially available immuno-histostaining kit (Zymed's HistoMouse™ SP Kit) utilizing biotin goat anti-mouse IgG, peroxidase streptavidin, and diaminobenzidine as substrate, except that the blocking reagent from the kit was replaced with the blocking materials indicated below.

The following procedure was followed.

1. BrdU labeled small intestine tissues were fixed in ethanol or 10% buffered formalin, paraffin embedded and 5 μm sections were prepared and affixed to a glass slide.

2. Each test slide was treated with one of the following "blocking" solutions:
  PBS (10 mM phosphate buffered saline, pH 7.4)
  10 normal goat serum/PBS
  1% BSA/PBS
  0.1casein/PBS The slides were incubated for 30 minutes, followed by three washings with PBS, at 2 minutes for each washing.

3. All the test slides except for the negative control slides, were incubated with Biotin linked goat anti-mouse IgG for 10 minutes at room temperature, followed by 3 washes with PBS, 2 minutes for each wash.

4. The slides, including the negative control slides, were incubated with peroxidase linked to streptavidin for 10 minutes at room temperature, followed by 3 washes with PBS, 2 minutes for each wash.

5. All slides were then developed with Diaminobenzidine substrate solution for 5 minutes at room temperature. The results are summarized in Table 1.

TABLE 1

Background Staining of fixed paraffin embedded tissue sections using conventional blocking agents

| | | | *Background staining | |
|---|---|---|---|---|
| Slide | Blocking | Biotin Gt x Mouse IgG | Alcohol fixed tissue | Alcohol fixed tissue |
| Negative control | PBS | No | – | – |
| Test #1 | PBS | Yes | ++++ | +++ |
| Test #2 | 10% Normal goat serum | Yes | +++ | ++ |
| Test #3 | 1% BSA | Yes | +++ | ++ |
| Test #4 | 0.1% Casein | Yes | +++ | ++ |

*The staining intensity grading system: – (negative), –/+ (minimum), + (weak), ++ (medium), +++ strong, ++++ (Very strong)

As may be seen from the results in Table 1, conventional blocking solutions, e.g. serum, BSA and casein, only reduced the background staining slightly.

EXAMPLE 2

Effect of Fab fragment of anti-immunoglobulin antibody on the reduction of background staining.

A purpose of this Example was to study the effect of various concentrations of Fab fragments of anti-immunoglobulin on reducing background staining.

The tissues used were either alcohol fixed or formalin fixed, BrdU treated mouse small intestine.

The detection system was as an immuno-histostaining kit utilizing biotin linked goat anti-mouse IgG, peroxidase linked to streptavidin, and diaminobenzidine as substrate (Zymed's HistoMouse™ SP), except that the blocking reagent was replaced as indicated below.

The following procedure was followed.

1. BrdU labeled small intestine tissues were fixed in ethanol or 10% buffered formalin, paraffin embedded and 5 μm sections were prepared and affixed to glass slides.

2. Each test slide was treated with one of the following blocking solutions:

10% normal goat serum

Fab fragment of goat anti-mouse IgG 10 μg/ml in 10% normal goat serum

Fab fragment of goat anti-mouse IgG 20 μg/ml in 10% normal goat serum

Fab fragment of goat anti-mouse IgG 40 μg/ml in 10% normal goat serum

Fab fragment of goat anti-mouse IgG 100 μg/ml in 10% normal goat serum

Fab fragment of goat anti-mouse IgG 200 μg/ml in 10% normal goat serum

Fab fragment of goat anti-mouse IgG 400 μg/ml in 10% normal goat serum

The slides were incubated for 30 minutes, followed by 3 washings with PBS, 2 minutes per wash.

3. All the test-slides except for negative control slides, were incubated with Biotin goat anti-mouse IgG for 10 minutes at room temperature, followed by 3 washes with PBS, 2 minutes each wash.

4. The slides, including the negative control slide, were incubated with peroxidase streptavidin for 10 minutes at room temperature, followed by 3 washes with PBS, at 2 minutes each wash.

5. All the slides were developed with Diaminobenzidine substrate solution for 5 minutes at room temperature. The results are summarized in Table 2.

TABLE 2

Effect of Fab fragment of anti-immunoglobulin antibody on reduction of background staining of fixed embedded tissue sections

| | Concentration of Fab anti-mouse IgG in 10% normal goat serum (μg/ml) | *Background staining | |
|---|---|---|---|
| Slide | | Alcohol fixed tissue | Formalin fixed tissue |
| Test #1 | 0 | +++ | ++ |
| Test #2 | 10 | +++ | ++ |
| Test #3 | 20 | +++ | ++ |
| Test #4 | 40 | ++ | + |
| Test #5 | 100 | ++ | + |
| Test #6 | 200 | ++ | + |
| Test #7 | 400 | ++ | + |

*The staining intensity grading system: – (negative), –/+ (minimum), + (weak), ++ (medium), +++ strong, ++++ (Very strong)

The results in Table 2 are indicative that treatment with a monovalent antibody, e.g. Fab fragment anti-immunoglobulin antibody treatment, even at very high concentrations, does not abolish all the background staining presumably due to endogenous immunoglobulins in the specimen.

EXAMPLE 3

Effect of cross-linking of Fab fragments of anti-immunoglobulin antibody to the tissue sample on the reduction of background staining.

The effect on the reduction of background staining by cross-linking the monovalent antibody and the tissue to which it was immunologically bound was tested. In these tests the concentration of the cross-linking reagent was varied, and the concentration of monovalent antibody used to treat the tissue was optimal.

More specifically, a Fab fragment of anti-immunoglobulin was used at a concentration of 40 μg/ml. The concentration of the cross-linker, glutaraldehyde, was varied from a range of 0% to 2%.

The tissues used in the tests were either alcohol fixed or formalin fixed, BrdU treated mouse small intestine.

The detection system was an immuno-histostaining kit utilizing biotin linked to goat anti-mouse IgG, peroxidase streptavidin, and diaminobenzidine as substrate.

The following procedure was followed.

1. BrdU labeled small intestine tissues were fixed in ethanol or 10% buffered formalin, paraffin embedded and 5 micron sections were prepared and affixed to glass slides.

2. All the test slides were treated with Fab fragment of goat anti-mouse IgG in 10% normal goat serum. The slides were incubated for 30 minutes, followed by 3 washes with PBS, 2 minutes per wash.

3. The test slides were incubated with glutataldehyde at following concentrations: 0, 0.01%, 0.025%, 0.05%, 0.1%, 1% and 2% (v/v) in PBS.

4. The test slides were incubated with Biotin linked to goat anti-mouse IgG for 10 minutes at room temperature, followed by 3 washes PBS, 2 minutes per wash.

5. The slides were then incubated with peroxidase streptavidin for 10 minutes at room temperature followed by 3 washes with PBS, 2 minutes per wash.

6. All slides were developed with Diaminobenzidine substrate solution for 5 minutes at room temperature.
The results are summarized in Table 3.

TABLE 3

Effect of concentration of the cross-linking reagent on the reduction of background staining.

| | Concentration of | *Background staining | |
|---|---|---|---|
| Slide | glutaraldehyde in PBS (% volume/volume) | Alcohol fixed tissue | Formalin fixed tissue |
| Test #1 | 0 | ++ | + |
| Test #2 | 0.01 | + | +/− |
| Test #3 | 0.025 | − | − |
| Test #4 | 0.05 | +/− | +/− |
| Test #5 | 0.1 | + | + |
| Test #6 | 1.0 | ++ | + |
| Test #7 | 2.0 | ++ | + |

*The staining intensity grading system: − (negative), (minimum), + (weak), (medium), +++ strong, ++++ (Very strong)

The optimum concentration of cross-linker, glutaraldehyde, is 0.025% (v/v) in PBS. At this concentration, the background staining can be completely eliminated. However, background staining is also significantly reduced in a range of 0.01 to 0.05% glutaraldehyde.

EXAMPLE 4

Specific staining with mouse anti-BrdU primary antibody in the presence of Fab fragment of anti-immunoglobulin antibody and cross-linker Subsequent to cross-linking monovalent antibody to tissue, specific binding of antibody to the treated tissue specimen was tested using mouse anti-BrdU as the primary antibody. This antibody binds to BrdU which has been incorporated into nucleic acids in cells. The optimum concentration of this primary antibody was previously established The tissues tested were either alcohol fixed or formalin fixed, BrdU treated mouse small intestine.

The detection system was an immuno-histostaining kit utilizing biotin linked to goat anti-mouse IgG, peroxidase streptavidin, and diaminobenzidine. as substrate.

The procedure used was the following.

1. BrdU labeled small intestine tissues were fixed in ethanol or 10% buffered formalin, paraffin embedded and 5 μm sections were prepared and affixed to glass slides.

2. All the slides were treated with Fab fragment of goat anti-mouse IgG at 40 μg/ml in 10% normal goat serum. The slides were incubated for 30 minutes, followed by 3 washes with PBS, .2 minutes per wash.

3. All the slides were incubated 10 minutes with the cross-linker (glutaraldehyde) at a concentration of 0.025% (v/v) in PBS, followed by 3 washes with PBS, 2 minutes per wash.

4. Test slides were incubated with mouse anti-BrdU antibody in 10% normal goat serum, at 10 micrograms/ml, a concentration previously determined to be optimum.

5. Negative control slides were incubated with 10% normal goat serum without mouse anti-BrdU antibody.

6. All the slides were subsequently incubated with Biotin linked to goat anti-mouse IgG for 10 minutes at room temperature, followed by 3 washes with PBS, 2 minutes per wash.

7. All the slides were then incubated with peroxidase streptavidin for 10 minutes at room temperature, followed by 3 washes with PBS, 2 minutes per wash.

8. All the slides were developed with Diaminobenzidine substrate solution for 5 minutes at room temperature.

The results are summarized in Table 4.

TABLE 4

Specific staining of bromo-dU tissue with anti-bromo-dU antibody in tissue to which monovalent antibody has been cross-linked

| | | *Specific staining/ background staining | |
|---|---|---|---|
| Slide | Mouse anti-BrdU primary antibody | Alcohol fixed tissue | Formalin fixed tissue |
| Negative control | No | −/− | −/− |
| Test slide | Yes | ++++/− | ++++/− |

*The staining intensity grading system: − (negative), −/+ (minimum), + (weak), ++ (medium), +++ strong, ++++ (Very strong)

The results in Table 4 indicate that the combination treatment of tissue specimens with Fab antibody and cross-linking reagent does not in any way hinder the specific binding of a primary antibody to its antigen in the specimen.

EXAMPLE 5

Preparation of SH-blocked Fab' Goat-Antimouse IgG (H+L)

Fab' with blocked sulfhydryl groups was prepared from goat antimouse IgG as follows.

Goat antimouse IgG was digested with pepsin at pH 4.0 for 24 hours at 37° C. The resulting (Fab')$_2$ fragments were purifed by gel filtration on AcA34 ultragel. The purified fragments were reduced with 20 mM mercaptoethylamine at pH 6.0, room temperature for two hours. Excess reducing agent was then removed by passage of the reaction mixture through a G-25 Sephadex column, using sodium phosphate buffer, pH 6.5. The column isolated Fab' was treated with N-ethylmaleimide, 20 mM, for two hours at room temperature, and then dialyzed against phosphate buffered saline to remove excess N-ethyl maleimide.

We claim:

1. An immunoassay method for detecting a target moiety in a biological sample suspected of containing the target moiety, wherein the target moiety is detected by incubating the biological sample with a targeting antibody that binds the target moiety and subsequently with a detecting antibody system containing a label that detects the presence of the targeting antibody, and wherein the biological sample contains a non-targeted antigenic determinant recognized by at least one antibody in the detecting antibody system F, the improvement in the method comprising prior to incubating the biological sample with the targeting antibody, performing the following steps in the following order:

(a) incubating the biological sample with a monovalent antibody that recognizes an antigenic determinant recognized by the detecting antibody system under conditions that allow immunological binding to the non-targeted antigen in the biological sample and removing excess monovalent antibody; and (b) cross-linking an immunological complex formed in step (a); wherein the performance of steps (a) and (b) causes an increase in specific binding relative to non-specific binding by the detecting antibody system.

2. An immunoassay according to claim 1 wherein the biological sample is affixed to a solid substrate.

3. An immunoassay according to claim 1 wherein the cross-linking reagent is an aldehyde.

4. An immunoassay according to claim 2 wherein the cross-linking reagent is an aldehyde.

5. An immunoassay according to claim 3 wherein the aldehyde is selected from the group consisting of paraformaldehyde, glutaraldehyde, and formaldehyde.

6. An immunoassay according to claim 4 wherein the aldehyde is selected from the group consisting of paraformaldehyde, glutaraldehyde, and formaldehyde.

7. An immunohistochemical method for detecting a target moiety in a biological sample suspected of containing the target moiety, wherein the target moiety is detected by incubating the biological sample with a targeting antibody that binds the target moiety and subsequently with a detecting antibody system containing a label that detects the presence of the targeting antibody, and wherein the biological sample contains a non-targeted antigenic determinant recognized by at least one antibody in the detecting antibody system F, the improvement in the method comprising prior to incubating the biological sample with the targeting antibody, performing the following steps in the following order:

(a) incubating the biological sample with, a monovalent antibody that recognizes an antigenic determinant recognized by the detecting antibody system under conditions that allow immunological binding to the non-targeted antigen in the biological sample and removing excess monovalent antibody; and (b) cross-linking an immunological complex formed in step (a); wherein the performance of steps (a) and (b) causes an increase in specific binding relative to non-specific binding by the detecting antibody system.

8. The method of claim 7 wherein the label is an enzymic moiety.

9. The method of claim 8 wherein the enzymic moiety label in the presence of enzyme substrate catalyzes a reaction yielding a product that stains tissue, and a complex containing the detecting antibody is detected by the presence of stain.

10. The method of claim 9 wherein the enzymic moiety catalyzes a horseradish peroxidase reaction.

* * * * *

UNITED STATES PATENT AND TRADEMARK OFFICE
CERTIFICATE OF CORRECTION

PATENT NO. : 5,869,274
DATED : February 9, 1999
INVENTOR(S) : Dean TSAO et al.

It is certified that error appears in the above-identified patent and that said Letters Patent is hereby corrected as shown below:

On the title page, item [56]:

Page 1, in "Other Publications", delete "Foulds et al." reference. This was cited twice.

Column 6, line 22, "bis" should be --*bis*--.

Column 10, lines 33-34, "Effect of cross-linking of Fab fragments of anti-immunoglobulin antibody to the tissue sample on the reduction of background staining" should be --Effect of cross-linking of Fab fragments of anti-immunoglobulin antibody to the tissue sample on the reduction of background staining--.

Column 10, line 59, "glutataldehyde" should be --glutaraldehyde--.

UNITED STATES PATENT AND TRADEMARK OFFICE
CERTIFICATE OF CORRECTION

PATENT NO. : 5,869,274
DATED : February 9, 1999
INVENTOR(S) : Dean TSAO et al.

It is certified that error appears in the above-identified patent and that said Letters Patent is hereby corrected as shown below:

Column 12, lines 24-25, "Preparation of SH-blocked Fab' Goat-Antimouse IgG (H+L) should be --Preparation of SH-blocked Fab' Goat-Antimouse IgG (H+L)--.

Column 12, line 48 "F" should be --but not recognized by the targeting antibody--.

Column 13, line 16 "F" should be --but not recognized by the targeting antibody--.

Signed and Sealed this

Seventh Day of September, 1999

Attest:

Q. TODD DICKINSON

Attesting Officer

Acting Commissioner of Patents and Trademarks